(12) United States Patent
Yasui et al.

(10) Patent No.: US 7,605,371 B2
(45) Date of Patent: Oct. 20, 2009

(54) HIGH-RESOLUTION HIGH-SPEED TERAHERTZ SPECTROMETER

(75) Inventors: Takeshi Yasui, Osaka (JP); Tsutomu Araki, Osaka (JP); Eisuke Saneyoshi, Osaka (JP)

(73) Assignee: Osaka University, Osaka (JP)

( * ) Notice: Subject to any disclaimer, the term of this patent is extended or adjusted under 35 U.S.C. 154(b) by 123 days.

(21) Appl. No.: 11/885,335

(22) PCT Filed: Aug. 30, 2005

(86) PCT No.: PCT/JP2005/015791

§ 371 (c)(1), (2), (4) Date: Aug. 30, 2007

(87) PCT Pub. No.: WO2006/092874

PCT Pub. Date: Sep. 8, 2006

(65) Prior Publication Data
US 2008/0165355 A1    Jul. 10, 2008

(30) Foreign Application Priority Data
Mar. 1, 2005    (JP)    ............................. 2005-055367

(51) Int. Cl.
G01J 3/02    (2006.01)
(52) U.S. Cl. .................. 250/341.8; 250/341.1
(58) Field of Classification Search .............. 250/341.1, 250/341.8
See application file for complete search history.

(56) References Cited
U.S. PATENT DOCUMENTS
5,778,016 A * 7/1998 Sucha et al. ................ 372/38.1

6,414,473 B1 * 7/2002 Zhang et al. ................... 324/96
6,573,700 B2 * 6/2003 Zhang et al. ................... 324/96
2003/0001558 A1 * 1/2003 Zhang et al. ................... 324/96
2007/0194253 A1 * 8/2007 Nishizawa et al. ....... 250/493.1

FOREIGN PATENT DOCUMENTS
JP    A-10-096610    4/1998
JP    A-2003-518617    6/2003
WO    WO 01/48457    7/2001

OTHER PUBLICATIONS
International Search Report of the International Searching Authority mailed on Oct. 18, 2005 for the corresponding International patent application No. PCT/JP2005/015791.

(Continued)

*Primary Examiner*—David P Porta
*Assistant Examiner*—Mark R Gaworecki
(74) *Attorney, Agent, or Firm*—Posz Law Group, PLC

(57) ABSTRACT

The mode-locking frequencies of two femtosecond laser light sources are controlled so that they are stabilized at high degree and the difference between the mode-locking frequencies is constant. The output of the laser light sources are used as a pumping light for generating terahertz pulses and a probe pulse light for terahertz detection. Since the time delay timings of the terahertz pulses and the probe pulse light the pulse periods of which are slightly different from each other shift from each other and the difference increases. Therefore, the temporally expanded terahertz pulses are measured by high-speed sampling without using any mechanical stage for time delay scanning. The terahertz electric field time waveform measured by high-speed sampling with the measurement time window of the pulse period is subjected to time-scale conversion and Fourier transform.

7 Claims, 12 Drawing Sheets

OTHER PUBLICATIONS

Naganori Saneyoshi et al., "Hikari Sampling-shiki Terahertz Jikan Ryoiki Bunkoho (I)—Femto-byo Hikari Sampling Kogen no Kaihatsu," The 65$^{th}$ Japan Society of Applied Physics, No. 3 (Sep. 1, 2004), pp. 985 (English Abstract provided).

Naganori Saneyoshi et al, "Hidoki Hikari Sampling-shiki Terahertz Jikan Ryoiki Bunkoho no Tameno Femto-byo Hikari Sampling Kogen no Kaihatsu," Optics Japan 2004 Koen Yokoshu (Nov. 4, 2004), pp. 372-373 (English Abstract provided).

Takeshi Yasui et al., "Highly-functional in process monitoring of a painting film by use of a terahertz electromagnetic pulse," Heisei 16 Nendo Kenkyu Josei Jigyo Seika Hokokukai Yokoshu Sangyo Gijutsu Kenkyu Josei Jigyo Heisei 14 Nendo Saitaku (Syuryobun nomi) Heisei 15 Nendo Keizoku Kenkyo, vol. 2, (2004) pp. 80-85 (English Abstract provided).

T. Yasui et al., "Asynchronous optical sampling for terahertz time-domain spectroscopy for ultrahigh spectral resolution and rapid data acquisition," Applied Physics Letter, vol. 87, Issue 6 (Aug. 1, 2005), Article 061101.

C. Janke et al., "Asynchronous optical sampling for high-speed characterization of integrated resonant THz-biosensors," Optics Letters, vol. 30, No. 11 (Jun. 1, 2005), pp. 1405-1407.

* cited by examiner

Temporal waveform of THz electric field

THz amplitude spectrum (a)　　　　　　　　　　　　(b)

HIGH-RESOLUTION HIGH-SPEED TERAHERTZ SPECTROMETER

FIELD OF THE INVENTION

The present technique relates to a terahertz spectroscopy technique using a terahertz electromagnetic pulse (referred to as a THz pulse, hereinafter) and to a measuring technique for performing high-speed high-resolution measurement of broadband spectrum of a THz pulse with spectral resolution equal to a laser mode-locked frequency, which is a theoretical limit in THz time-domain spectroscopy.

BACKGROUND OF THE INVENTION

Conventionally, a terahertz time-domain spectroscopy (referred to as a THz-TDS method, hereinafter) is known as a typical spectroscopy method using a THz pulse. FIG. 1 shows a typical experimental system configuration according to a THz-TDS method. In this method, first, temporal waveform of a pulsed THz electric field is measured by a pump-probe measurement (or cross-correlation measurement) using a THz pulse and a probe pulse light. The pump-probe measurement is a technique in which as shown in FIG. 2, the timing that the THz pulse and the probe pulse light overlap each other is sequentially shifted by time-delay scanning using a mechanical stage, and in which electric field of THz pulse sampled with the pulse width of the probe pulse light at each overlapped timings is measured on by one so that an ultrafast temporal waveform is reconstructed which cannot be measured in real time.

Further, in the THz-TDS method, Fourier spectra of THz amplitude and phase are obtained for spectroscopy measurement by performing Fourier transform calculation of the temporal waveform of THz electric field with a computer.

FIG. 3 shows the frequency spectrum of the THz amplitude obtained by performing, with a computer, Fourier transform calculation on the measured temporal waveform of THz electric field. Here, when the measured time window is denoted by T, the frequency resolution of the THz amplitude spectrum is expressed by 1/T.

That is, the frequency resolution is determined by the measured time window T of the THz electric field (amount of time-delay scanning), and hence is restricted by the moving stroke length (L) of time delay scanning (a mechanical stage) of FIG. 1. On the other hand, the frequency range is given by the inverse (1/t) of unit increment of time-delay scanning stage (t).

Thus, in the conventional THz-TDS method based on the mechanical time-delay scanning, there is an inherent trade-off between improvement of frequency resolution and a reduction in measuring time.

DISCLOSURE OF THE INVENTION

Problems to be Solved by the Invention

In the conventional THz-TDS method, as described above, the frequency resolution is determined by the inverse of the measured time window T (that is, amount of time delay scanning) of the temporal waveform of a THz electric field. This is, in practice, restricted by the moving stroke length (L) of the mechanical stage provided in the spectroscopy device.

The largest measured time window of the THz-TDS method, in which only one THz pulse in a successive THz pulse sequence (frequency=$f_0$) is allowed to fall within the measured time window T, is the pulse period (=1/$f_0$) (FIG. 3). When the frequency resolution achieved by this largest measured time window (=pulse period) is defined as a theoretical limitation of frequency resolution, the value is equal to the mode-locked frequency (=$f_0$) of the femtosecond laser on the basis of the inverse of the pulse period. The stroke length (L) of the mechanical stage necessary for realizing time delay equal to pulse period is defined by the following Formula 1. Here, c denotes the speed of light.

$$L = \frac{c}{2f_0} \qquad \text{[Formula 1]}$$

On the other hand, the mode-locked frequency ($f_0$) of the femtosecond laser is defined by the following formula. Here, l denotes the cavity length of femtosecond laser.

$$f_0 = \frac{c}{2l} \qquad \text{[Formula 2]}$$

Substituting Formula 2 into Formula 1, the following Formula 3 is derived.

$$L = \frac{c}{2f_0} = \frac{c}{2\left(\frac{c}{2l}\right)} = l \qquad \text{[Formula 3]}$$

Thus, in order to achieve the theoretical limitation of frequency resolution in the conventional THz-TDS method using a mechanical stage, stage scanning along a length equal to the laser cavity length (usually, approximately 1.5 to 2 m) is necessary.

However, mechanical stage scanning of such a long stroke is not practical owing to the problem of the device and the measuring time. Actually, the frequency resolution is determined from the stroke length (1 cm to 10 cm or the like) of the usual mechanical stage. This is a frequency resolution inferior to the theoretical limitation of frequency resolution by a factor of 10 to 100 or the like.

Further, even when a other spectroscopic techniques, such as Fourier transform infrared spectrometer or a diffraction type spectrometer, are employed, a frequency resolution on the order of the mode-locked frequency is difficult to be achieved.

An object of a high-resolution/high-speed terahertz spectrometer according to the present invention is to provide a measuring device capable of performing THz spectroscopy with the theoretical limitation of frequency resolution (=mode-locked frequency) at a high speed.

Means for Solving the Problem

In order to resolve the above-mentioned problem, the present invention provides a high-resolution/high-speed terahertz spectrometer capable of performing THz spectroscopy with the theoretical limitation of frequency resolution (=mode-locked frequency) at a high speed.

A first aspect of the present invention provides a high-resolution/high-speed terahertz spectrometer comprising:

(a) two units of femtosecond laser means each having a laser repetition rate (mode-locked frequency) slightly different from each other;

(b) mode-locked frequency controlling means for controlling the two units of femtosecond laser means such that the mode-locked frequency of each of the two units of femtosecond laser means is stabilized at a high degree and the difference in the mode-locked frequencies is held at a predetermined fixed value;

(c) terahertz wave radiating means for emitting a terahertz electromagnetic pulse by using output light of one femtosecond laser as excitation light and by using a photoconductivity switch or a nonlinear optical crystal;

(d) terahertz wave optical system means for irradiating a sample for spectroscopy with a terahertz electromagnetic pulse emitted from the terahertz wave radiating means and further guiding the terahertz electromagnetic pulse influenced by the sample;

(e) terahertz wave detecting means for detecting an temporal waveform of electric field of the terahertz electromagnetic pulse by using output light of the other femtosecond laser as probe pulse light, by making incident the terahertz electromagnetic pulse and probe pulse light, and by using a photoconductive switch or an electro-optical sampling method;

(f) trigger signal generating means for generating a time origin signal by extracting a part of the output light of the two units of the femtosecond laser means; and (g) signal waveform measuring means for performing high-speed measurement free from influence of timing jitter, by amplifying the weak electric signal outputted from the terahertz wave detecting means, by using as a time origin signal the signal outputted from the trigger signal generating means and by detecting in synchronization a signal waveform of the terahertz electromagnetic pulse.

When two femtosecond laser light sources are used respectively for THz pulse generation and probe pulse light while the femtosecond lasers are controlled such that the mode-locked frequencies of the two laser light sources are stabilized at a high degree and the difference in the mode-locked frequencies is held at a predetermined fixed value, the timing that the THz pulse and the probe pulse light overlap each other shifts automatically at every pulse. This permits omission of a mechanical stage for time delay scanning and hence simultaneous realization of the largest measuring time window and a rapid measurement.

A second aspect of the present invention provides the high-resolution/high-speed terahertz spectrometer according to the first aspect, characterized in that in the constituent means (b) of the first aspect, the mode-locked frequency controlling means perform control by using as a reference signal an electric signal outputted from a frequency standard device and by using as a control signal a fundamental wave or a higher harmonic component of the mode-locked frequency.

A third aspect of the present invention provides the high-resolution/high-speed terahertz spectrometer according to the second aspect, characterized in that the frequency standard device is a rubidium frequency standard device or a cesium frequency standard device.

A fourth aspect of the present invention provides the high-resolution/high-speed terahertz spectrometer according to any one of the first to the third aspects, characterized in that in the constituent means (f) of the first aspect, the trigger signal generating means is a device for extracting a part of the output light of the two units of the femtosecond laser means, non-collinearly focusing the light onto a nonlinear optical crystal, and performing photoelectric conversion of the generated SFG (sum frequency generation light) cross-correlation signal light so as to output the light.

A fifth aspect of the present invention provides the high-resolution/high-speed terahertz spectrometer according to any one of the first to the fourth aspects, characterized by further comprising (h) signal analyzing means for acquiring frequency analysis information of a sample from a high-resolution Fourier spectrum (frequency spectrum in amplitude and phase) obtained by performing scale conversion of time axis with respect to a temporal waveform of terahertz electromagnetic pulse outputted from the signal waveform measuring means and by performing Fourier transform thereon.

A sixth aspect of the present invention provides the high-resolution/high-speed terahertz spectrometer according to any one of the first to the third aspects, characterized in that the mode-locked frequency controlling means is controlling means for a cavity length of the femtosecond laser.

The mode-locked frequency of a femtosecond laser is determined by the laser cavity length. However, this frequency fluctuates depending on environmental artifacts such as temperature change, air disturbance, and vibration. This is because the optical cavity length of the laser fluctuates depending on the above-mentioned factors. Thus, when ultra-precise control is performed on the mechanical cavity length of the femtosecond laser corresponding to such fluctuation, stabilization control is achieved in the mode-locked frequency.

A seventh aspect of the present invention provides the high-resolution/high-speed terahertz spectrometer according to any one of the first to the third aspects, characterized in that a frequency range, a sampling time, or a time scale expansion factor can be set up arbitrarily by selecting the value of the frequency difference held by the mode-locked frequency controlling means.

EFFECT OF THE INVENTION

The femtosecond laser light used for the THz pulse generation is a pulse sequence having a mode-locked period ($=1/f_0$) in the time domain (see FIG. 4($a$)). However, in the optical frequency domain which is related to Fourier transform, the laser light has a spectrum structure in which a sequence of a large number of stable optical frequency modes aligns regularly at intervals of mode-locked frequency ($=f_0$) around a particular center frequency (e.g., 375 THz in a femtosecond titanium sapphire laser) (see FIG. 4($b$)). Such alignment of a frequency mode sequence in the shape of a comb (comb) is referred to as a frequency comb. In particular, a frequency comb in the optical region is referred to as an optical comb.

On the other hand, the THz pulse generation using a femtosecond laser and a photoconductivity switch (or a nonlinear optical effect) can be interpreted as broadband demodulation of a mode-locked pulse sequence via the photoconductive switch. Thus, the THz pulse sequence synchronized with the femtosecond laser light in the time domain (see FIG. 5($a$)) is, in the frequency domain, observed in the form that a power spectrum in which the fundamental component of mode-locked frequency ($=f_0$) and a large number of higher harmonic components align like a comb (comb) at regular intervals from the zero frequency is down-converted into the radio wave region (see FIG. 5($b$)). This is referred to as an RF (Radio Frequency) comb.

The RF comb is expanded into the terahertz region by virtue of the ultra high-speed response of the photoconductive switch (or the nonlinear optical effect). Such an RF comb in the terahertz region is defined as a THz comb in the present specification.

The frequency intervals of the frequency modes in the sequence that constitute the THz comb are equal to the mode-locked frequency. Thus, when a frequency resolution equal to the mode-locked frequency is achieved, the envelope of each single component peak in the frequency mode sequence that constitutes the THz comb can be extracted and detected.

As such, the THz comb has features such as wide frequency selectivity, remarkably high spectral purity, direct absolute frequency calibration, frequency multiplication functionality, and simplicity. Thus, a frequency mode sequence extracted from a stabilized THz comb obtained by stabilizing the above-mentioned comb at a high degree has stability not only in frequency but also in phase and intensity. Accordingly, a high-quality THz wave can be provided. Thus, when such a stabilized THz comb can be used as a frequency ruler in the THz region, this comb is expected to serve as remarkably useful means in next-generation information communication, frequency standard, and high-resolution terahertz spectroscopy.

The high-resolution/high-speed terahertz spectrometer according to the present invention is a measuring technique that permits arbitrary extraction/selection and detection of a single frequency mode from a THz comb. The present invention has an effect that, for example, when applied to next-generation information communication, the spectrometer can be used as a frequency analyzer (decoder) for THz-band wavelength multiplex communication having the number of wavelength channels equal to the number of frequency modes (10,000 or more per 1 THz in the THz spectrum band).

Further, an effect is obtained that the spectrometer can serve as a metrological device when the THz comb is used as a frequency standard in the terahertz band for bridging the light wave and the electric wave. Furthermore, an effect is obtained that the spectrometer can serve as a physical property evaluating device for semiconductor and the like by means of high-resolution terahertz spectrometry.

BEST MODE OF CARRYING OUT THE INVENTION

A high-resolution terahertz spectrometer according to the present invention is described below in detail with reference to the drawings and with comparing a usual THz-TDS measuring device employing a mechanical time-delay stage.

In the configuration of a measuring device employing a general THz-TDS method, as shown in FIG. 1, one unit for femtosecond laser light is used for both of pumping light (THz pulse generation) and probe pulse light (THz pulse detection). Thus, both are always in synchronization. Accordingly, in the THz-TDS method, time delay scanning is performed by a mechanical stage so that temporal timing where the two pulses overlap each other in a THz detector is shifted sequentially. In this state, cross-correlation measurement is performed (a pump-probe method). Finally, temporal waveform of a terahertz pulse is reproduced.

FIG. 2 shows a situation in which two operations of time delay scanning are performed by means of movement of the mechanical stage and three points are measured so that a THz waveform is reconstructed. Here, in actual measurement, measurement is performed at measurement points of a larger number so that a THz waveform is reconstructed.

On the other hand, FIG. 6 shows a configuration diagram of a high-resolution/high-speed terahertz spectrometer according to the present invention. The mode-locked frequencies of the two lasers are controlled such that the mode-locked frequencies of both of a femtosecond laser 1 (mode-locked frequency=$f_1$) and a femtosecond laser 2 (mode-locked frequency=$f_2$) are stabilized at a high degree and the difference ($\otimes=f_2-f_1$) in the mode-locked frequencies is fixed at a particular value. Here, this is referred to as a femtosecond light sampling light source. Then, in this configuration, both laser lights are used respectively as pumping light for THz pulse generation and probe pulse light. Further, a part of both laser lights are respectively extracted and used in trigger signal generating means (e.g., an SFG (sum frequency generation light) intensity-cross correlation meter).

FIG. 7 shows a schematic diagram describing a situation that a terahertz temporal waveform is reproduced in the high-resolution/high-speed terahertz spectrometer according to the present invention. Individual pulse periods of the THz pulse and the probe pulse light generated by the femtosecond light sampling light source differ slightly from each other. Thus, the timing that the THz pulse and the probe pulse light overlap each other shifts automatically at every pulse. Here, the THz pulse period is denoted by $1/f_2$, while the probe pulse period is denoted by $1/f_1$. Then, the time interval (sampling period SI) by which shift occurs at every pulse is defined by the following Formula 4.

$$SI = \frac{1}{f_1} - \frac{1}{f_2} = \frac{\Delta}{f_1 f_2} \qquad \text{[Formula 4]}$$

The time (sampling time ST) elapsing from the state ((a) of FIG. 7) that the THz pulse and the probe pulse light overlap each other to the state ((b) of FIG. 7) that they overlap again after the automatic shifting of the overlapping timing at every pulse is defined by the following Formula 5. This time value indicates one operation of time delay scanning equal to the pulse period.

$$ST = \frac{1}{\Delta} \qquad \text{[Formula 5]}$$

The trigger signal generating means generates a time origin signal at each time when the THz pulse and the probe pulse light overlap each other ((a) and (b) of FIG. 7). When this signal is used as a trigger signal for the time origin, high-speed measurement of the signal waveform is achieved free from influence of timing jitter.

The temporal waveform of THz electric field acquired as described here is observed in the form expanded in time on the basis of the principles of an optical sampling method. The time-scale expansion factor (M) is defined by the following Formula 6.

$$M = \frac{f_2}{\Delta} \qquad \text{[Formula 6]}$$

When the temporal waveform obtained by the optical sampling measurement is converted at the above-mentioned time-scale expansion factor, a THz temporal waveform in the actual time scale is reproduced. When Fourier transform is performed on the THz temporal waveform having undergone scale conversion, frequency spectra in amplitude and phase are obtained. In this case, since time delay scanning having a period equal to the pulse period is performed always regardless of the sampling time ST, a frequency resolution equal to the mode-locked frequency which is the theoretical limitation of frequency resolution is always achieved. On the other hand, from the above-mentioned sampling period, the frequency range (FR) is defined by the following Formula 7.

$$FR = \frac{1}{SI} = \frac{f_1 f_2}{\Delta} \quad \text{[Formula 7]}$$

FIGS. 8, 9, and 10 show correlation graphs of the frequency range, the sampling time, and the time-scale expansion factor versus the mode-locked frequency difference ⊛in the two femtosecond lasers. Here, $f_1$ and $f_2$ are 80 MHz. When a frequency difference⊛is selected, the frequency range, the sampling time, and the time scale expansion factor can be set up arbitrarily.

As described above, in the high-resolution/high-speed terahertz spectrometer according to the present invention, different from the conventional THz-TDS measuring device, a mechanical stage is omitted. This provides an advantage that time delay scanning of the pulse period, that is, the theoretical limitation of frequency resolution (=mode-locked frequency), and rapid measurement are realized simultaneously. Further, when the mechanical stage is omitted, the optical system is simplified and hence size reduction is achieved in the device.

EXAMPLE 1

An example of the high-resolution/high-speed terahertz spectrometer according to the present invention is described below. FIG. 11 shows a block diagram of the high-resolution/high-speed terahertz spectrometer of the present example.

The high-resolution/high-speed terahertz spectrometer has been developed by employing a femtosecond laser 1 (mode-locked titanium sapphire laser, center wavelength 790 nm, mode-locked frequency 82.6 MHz, pulse width 100 fs) and a femtosecond laser 2 (mode-locked titanium sapphire laser, center wavelength 800 nm, mode-locked frequency 82.6 MHz, pulse width 10 fs). Here, the mode-locked frequencies of the femtosecond laser 1 and the femtosecond laser 2 are approximately the same. The femtosecond laser 2 was used for THz pulse generation, while the femtosecond laser 1 was used for probe pulse light. In the present example, for simplicity of the femtosecond light sampling light source, high-degree stabilization was not performed on the mode-locked frequencies of the two lasers. Instead, the mode-locked frequency of the femtosecond laser 1 was controlled such that the difference in the mode-locked frequencies of the two lasers is always fixed at a particular value (e.g., =100 Hz).

In the light sampling light source controlling unit of FIG. 11, heterodyne detection is performed, with a voltage-controlled oscillator, on two laser lights (beams) detected by a high-speed photodetector, so that the tenth higher harmonic component signals (826 MHz) of the mode-locked frequency are respectively beat down to a beat signal at or below 1 MHz. Furthermore, heterodyne detection is performed mutually on the two signals so that a difference frequency signal of the tenth higher harmonic is generated. This signal is used as a control signal. That is, the fluctuation in the mode-locked frequency is magnified by a factor of 10, and then the obtained signal is used as a control signal so that ultraprecision is achieved in the stabilization control.

Using as a reference signal the signal provided from a reference signal generator in the optical sampling light source controlling unit of FIG. 11, laser cavity length control is performed by a piezo-electric element attached to a resonator mirror of the femtosecond laser 1, such that the control signal (difference frequency signal of the tenth higher harmonic) is fixed at a particular value (=1 kHz). By virtue of this, the difference in the mode-locked frequencies (fundamental component) is always stabilized at 100 Hz.

FIG. 12 shows the difference frequency signal in the mode-locked frequencies of the two femtosecond laser light sources. As seen from the figure, in the free-run state (the state that stabilization control is not performed), the difference frequency fluctuates as time elapses. In contrast, in the locked state (the state that stabilization control is performed), the difference frequency is at a particular fixed frequency (97 Hz in FIG. 12). As such, high-resolution/high-speed terahertz spectrometry is achieved in a state that the mode-locked frequency difference in the two lasers is sufficiently stabilized.

A part of both laser lights having undergone the optical sampling stabilization control as described above are fed to an SFG (sum frequency generation light) intensity cross-correlation measuring unit which is used for the trigger signal generation (see FIG. 11). Both laser lights are non-collinearly focused on a nonlinear optical crystal by a lens. As a result, SFG intensity cross-correlation signal light of both laser lights is generated. Then, photoelectric detection is performed on this light by a photomultiplier. Then, after the weak current signal is amplified by a current preamplifier, the obtained signal is used as a time origin signal for the high-resolution/high-speed terahertz spectrometer.

Here, FIG. 13 shows an SFG (sum frequency generation light) cross-correlation waveform of the two femtosecond laser light sources obtained by the high-resolution/high-speed terahertz spectrometer of the present Example 1. FIG. 13 demonstrates a situation that the cross-correlation waveform is high-speed-sampled as a burst waveform by the probe pulse light. This SFG cross correlation signal is used as a time origin signal for the high-resolution/high-speed terahertz spectrometer.

As shown in FIG. 11, the remainders of both laser lights are fed to the THz-TDS unit. The femtosecond laser 2 is used for pumping light for THz generation, while the femtosecond laser 1 is used for a probe light for THz detection. A bow-tie type photoconductive switch was used for THz generation and detection. Here, the mode-locked frequencies of the THz pulse and the probe pulse light generated by the femtosecond optical sampling light source differ slightly (100 Hz) from each other. This permits high-speed sampling measurement (measurement period is 10 ms) of the temporal waveform of THz electric field in the time window equal to pulse period (12 ns) without the necessity of mechanical time-delay scanning (optical sampling method).

The current signal obtained by the high-speed sampling in the photoconductive switch for THz detection is amplified and low-pass-filtered by a current preamplifier, and then measured by a digital oscilloscope by using as a synchronization signal of the time origin generated by the SFG cross-correlation measuring unit.

FIG. 14(a) shows the THz temporal waveform obtained in the full pulse period by the high-resolution high-speed terahertz spectrometer of the present example, where 1000 times of accumulation is performed by the digital oscilloscope (measuring time 10 seconds, number of data points 25000). The scale of time axis is expanded in time by a factor of 826,000 (expansion factor=mode-locked frequency/frequency difference) on the basis of the principles of the optical sampling method (see the upper scale of the graph for the actual time scale of the oscilloscope).

FIG. 14(b) is an enlargement of FIG. 14(a). Since a narrow-band bowtie-type photoconductive switch is used in the THz generation and detection, the pulse width is broad. However, temporal waveform of the THz electric field is recognized.

FIG. 14(c) shows a temporal waveform of THz electric field (measuring time 5 minutes, number of data points 256) obtained by the conventional THz-TDS method (a time delay stage and a lock-in amplifier were used). When FIG. 14(c) is compared with FIG. 14(b), the features of the two waveforms almost coincide with each other. This demonstrates that the temporal shape of THz pulse is accurately acquired by the femtosecond optical sampling THz-TDS method. In the conventional method, since time delay scanning is performed by using a mechanical stage, the measuring time increases with an increasing amount of time delay (5 minutes*120=10 hours is necessary for obtaining a time waveform of the same scale as FIG. 14(a)). In contrast, according to the present technique, the measuring time does not depend on amount of the time delay, and is always fixed (10 seconds in this case). That is, a remarkable reduction is achieved in the measuring time.

FIG. 15 shows the temporal waveforms of the THz pulse obtained under different measurement time (10 ms, 100 ms, 1 s, 10 s), that is, different accumulation numbers (1 time, 10 times, 100 times, 1000 times). This figure demonstrates that the signal waveform can be acquired even by optical sampling measurement (measuring time 10 ms) of a single sweep. Further, the figure demonstrates that the high-speed accumulation processing improves the measurement SN ratio.

In the THz-TDS method, the temporal waveform of THz electric field is measured directly. Thus, by Fourier transforming the temporal waveform of THz electric field, frequency spectra (Fourier spectra) in amplitude and phase are obtained. FIG. 16(a) shows an amplitude spectrum obtained by Fourier transforming the temporal waveform of THz electric field of FIG. 14(a) (time window=pulse period=12 ns). As seen from the figure, since a narrow-band bowtie-type photoconductive switch is used for THz generation and detection, the spectrum bandwidth is restricted to approximately 0.5 THz. However, a remarkably high frequency resolution is achieved in the measurement.

For the purpose of comparison, an amplitude spectrum obtained by Fourier transforming the temporal waveform of THz electric field of FIG. 14(c) according to the conventional method is shown in FIG. 16(b). The comparison with each other demonstrates that the frequency resolution is improved remarkably in the present technique. This results from the difference between the two time-delay amounts. Even in the conventional method, when sufficiently long time-delay scanning is performed by the mechanical stage, a similar frequency resolution can be achieved. However, this requires a remarkably long measuring time (10 hours). In the present technique, the theoretical limitation of frequency resolution (=mode-locked frequency) is always achieved in a fixed time (10 seconds in this case).

Spectra of absorption and a refractive index are calculated respectively from the amplitude spectrum and the phase spectrum obtained as described here, and then the calculated spectra can be used in component analysis of the measurement object. Conventionally, spectral analysis methods using visible light and infrared light have been known. However, in these conventional methods, only intensity information, that is absorption, can be observed. In contrast, in the THz-TDS, identification can be performed on the basis of two parameters of the absorption and the refractive index (complex refraction index) specific to a substance. This improves the identification capability of the substance.

Further, when the above-mentioned spectrum is acquired with the theoretical limitation of frequency resolution by the high-resolution/high-speed terahertz spectrometer according to the present invention, identification characteristics for a substance are improved remarkably. Furthermore, when the sample position is also scanned, spectroscopic imaging can be realized. This can be applied to component analysis imaging.

Here, the procedure of component analysis using the THz amplitude and phase spectra obtained by Fourier transform of the temporal waveform of a THz pulse is described below. The temporal waveform E(t) of a THz pulse contains information of the amplitude and the phase of the THz pulse. Thus, when Fourier transform is performed on this information (see the following Formula 8), an amplitude spectrum E( ) and a phase spectrum ( ) are obtained.

$$E(\omega) = \frac{1}{2\pi} \int_{-\infty}^{\infty} E(t) \exp(i\omega t)\, dt = |E(\omega)| \exp[i\theta(\omega)] \quad \text{[Formula 8]}$$

First, a temporal waveform of THz pulse Er(t) in the case of absence of a sample is measured. Then, Fourier transform is performed on this by a computer so that an amplitude spectrum |Er( )| and a phase spectrum r ( ) are acquired. Next, Fourier transform is performed on a temporal waveform Es(t) in the case of presence of a sample so that an amplitude spectrum |Es( )| and a phase spectrum s( ) are acquired. This situation is schematically shown in FIG. 17.

Then, according to the procedure described in the following Formulas 9 to 11, an absorption spectrum k( ) and a refractive index spectrum n( ) are calculated (for details, see Spectroscopy Research, Vol. 50, No. 6, p. 273).

In the following Formulas 9 to 11, c denotes the speed of light, while d denotes the thickness of a sample. Further, FIG. 17 shows the case of transmission. However, the following formulas hold also in the case of reflection.

$$t(\omega) = \frac{E_s(\omega)}{E_r(\omega)} = \frac{|E_s(\omega)|}{|E_r(\omega)|} \exp[i\{\theta_s(\omega) - \theta_r(\omega)\}] \quad \text{[Formula 9]}$$

$$\frac{|E_s(\omega)|}{|E_r(\omega)|} = \frac{4n}{(1+n)^2} \exp\left(-\frac{k\omega}{c}d\right) \quad \text{[Formula 10]}$$

$$\theta_s(\omega) - \theta_r(\omega) = \frac{(n-1)\omega}{c}d \quad \text{[Formula 11]}$$

As such, in the THz-TDS method, a THz pulse having a broadband spectrum is used. By virtue of this, a substance can be identified from the frequency spectrum of the absorption and/or the refractive index obtained by performing Fourier transform on the temporal waveform of THz electric field. The conventional THz-TDS has a problem that although a broadband spectrum can be acquired by one time of mechanical time-delay scanning, a very high frequency resolution cannot be achieved. However, the high-resolution/high-speed terahertz spectrometer according to the present invention resolves the restriction concerning the frequency resolution and achieves the theoretical limitation of frequency resolution.

Each of substances such as medicines, illegal drugs, agricultural chemicals, vitamins, and sugars indicate a characteristic absorption spectrum (fingerprint spectrum) that allows substance identification in the THz region. Thus, when the absorption spectrum of a sample is compared with the fingerprint spectrum (known) for each substance component, a component contained in the sample can be specified. Further, in a case that the sample contains several kinds of components, each component can be analyzed by using fingerprint spectra and a principal component analysis method. In particular, when the theoretical limitation of frequency resolution is achieved by employing the high-resolution/high-speed terahertz spectrometer according to the present invention, identification characteristics for a substance in the method employing fingerprint spectra are improved remarkably.

EXAMPLE 2

In Example 2, ultra-broadband wavelength multiplex THz information communication technique employing a stabilized THz comb light source and a high-resolution/high-speed terahertz spectrometer is described, which is an application of the high-resolution/high-speed terahertz spectrometer according to the present invention. FIG. 18 shows a block diagram.

For the purpose to generate a broadband THz comb, a femtosecond laser 2 (mode-locked titanium sapphire laser, center wavelength 800 nm, mode-locked frequency 82.6 MHz, pulse width 10 fs) is employed that can generate ultrashort pulses.

When a pulse shaping technique is applied on the laser light, wavelength multiplex communication information can be carried on the spectrum of the optical comb which is a frequency comb in the optical region. The pulse shaping technique is described in detail in J. Y. Sohn, Y. H. Ahn, D. J. Park, E. Oh and D. S. Kim, Appl. Phys. Lett., Vol. 81, No. 1, pp. 13-15 (2002). Thus, description is omitted here.

As such, when THz generation is performed using an optical comb carrying wavelength multiplex modulation and a photoconductive switch (or a nonlinear optical crystal), the wavelength multiplex information on the optical comb is transferred to the THz comb. On the other hand, a femtosecond laser 1 (mode-locked titanium sapphire laser, center wavelength 790 nm, mode-locked frequency 82.6 MHz, pulse width 100 fs) and a photoconductive switch (or a nonlinear optical crystal) is employed for THz detection.

A THz comb is generated in a demodulation process for femtosecond optical comb via a photoconductive switch (or a nonlinear optical effect). Thus, when the mode-locked frequency of the femtosecond laser 2 is stabilized, a stabilized THz comb light source is realized. The 100th higher harmonic component (8.26 GHz) detected by a high-speed photodetector is extracted as a beat signal at or below 100 kHz by heterodyne detection performed with a frequency synthesizer synchronized with a rubidium frequency standard. When a stabilization control circuit that employs as a reference signal a signal from an arbitrary waveform generator synchronized with the rubidium frequency standard controls a cavity-mirror attaching piezo-electric element, high stabilization of the mode-locked frequency, that is, the THz comb, is achieved (a stabilized THz comb light source).

On the other hand, the mode-locked frequency of the femtosecond laser 2 for THz detection needs to be stabilized such that the frequency difference from the mode-locked frequency of the femtosecond laser 1 is always maintained at a fixed value. In an optical sampling stabilization control circuit (FIG. 11) like that of Example 1, stabilization with a difference frequency at or below 100 Hz is difficult owing to the problem of the control bandwidth. Thus, the time scale expansion factor is restricted to 826,000 at maximum.

Thus, in the configuration of FIG. 12, the optical sampling stabilization control system is changed so that stabilization can be performed arbitrarily even with a difference frequency at or below 100 Hz. Here, the control system for the femtosecond laser 1 for THz detection is changed into a control system similar to that for the femtosecond laser 2 for THz comb generation. Thus, the two independent control systems stabilize respectively the mode-locked frequencies of the laser light sources. Here, signals each having a frequency slightly different from each other are generated from the two arbitrary waveform generators synchronized with the same rubidium frequency standard, and then these signals are used respectively as reference signals for the high-degree stabilization control circuits of the lasers, so that simultaneous high stabilization of the mode-locked frequency and the difference frequency in the two lasers is achieved.

The remainders of both laser lights are fed to the THz-TDS unit. The femtosecond laser 2 is used for pumping light for THz generation, while the femtosecond laser 1 is used for probe light for THz detection. A photoconductive switch (or a nonlinear optical crystal) is used for THz generation and detection. The wavelength multiplex modulation of THz comb emitted from the photoconductive switch propagates through a free space (alternatively, a THz waveguide or a THz fiber), and is then detected by a photoconductive switch. Here, the mode-locked frequencies of the THz pulse and the probe pulse light generated by the femtosecond optical sampling light source differ slightly from each other. By virtue of this, high-speed sampling measurement can be performed on the temporal waveform of THz electric field of the pulse-period time window without the necessity of mechanical time-delay scanning (a optical sampling method). The weak current signal obtained by the high-speed sampling in the photoconductive switch for THz detection is amplified and low-pass-filtered by a current preamplifier. In wavelength multiplex information communication, when only the THz amplitude spectrum is necessary while the THz phase spectrum is unnecessary, the trigger signal generating means may be omitted. In this case, the THz amplitude spectrum is measured directly by a spectrum analyzer. As a result, the wavelength multiplex communication information carried on the THz comb is decoded.

EXAMPLE 3

Next, in Example 3, application to high-resolution/high-speed infrared time-domain spectrometry (IR-TDS) is described, which is an application of the high-resolution/high-speed terahertz spectrometer according to the present invention.

When a substance is irradiated with infrared light, infrared light of the same frequency as the proper molecular vibration is absorbed characteristically owing to the vibration and rotation of molecules constituting the substance. This provides an absorption spectrum that reflects the molecular structure sensitively. Since such an infrared absorption spectrum is a fingerprint spectrum characteristic to a molecular structure, an unidentified substance can be identified using this spectrum.

The Fourier transform infrared spectrometer which is used in typical infrared spectroscopy includes an infrared light source (a thermal light source or the like), a Michelson interferometer, and an infrared detector as shown in FIG. 19. In both cases of presence and absence of a sample, interference fringes (an interferogram) of infrared light are measured by the infrared detector causing a moving mirror to scan. Then, Fourier transform is performed on both, so that an infrared absorption spectrum is obtained. In the Fourier-transform infrared spectroscopy, in addition to no restriction with respect to the sample, abundant databases of standard fingerprint spectra in the infrared region are available. Thus, this method is used as substance identifying means in a wide range of applications. Similar to the conventional terahertz time-domain spectroscopy method, the spectral resolution is defined by the inverse of the stroke length of the mechanical stage that causes the moving mirror to scan. Thus, a long stage scanning is necessary for obtaining a high spectral resolution.

FIG. 20 shows an overall block diagram of an infrared time domain spectrometer. The device configuration is nearly identical to that of Example 1 (the configuration shown in FIG. 11). In the high-resolution/high-speed terahertz spectrometer of Example 1, when a photoconductivity switch or a nonlinear optical crystal is employed in the terahertz generating unit and the detection unit, a THz spectrum of 2 THz or the like is obtained comparatively easily.

On the other hand, when a nonlinear optical crystal (or an electro-optical crystal) having a sufficiently thin crystal thickness and a high infrared light generating efficiency (or detection efficiency) is used for infrared light generation and infrared light detection, the measurement bandwidth can be extended from the terahertz region to the infrared region. That is, elements in the terahertz generation and detection units are changed, the device can be used also in the infrared time-domain spectroscopy (IR-TDS). An explanation that the measurement bandwidth can be extended from the terahertz region to the infrared region is given in a paper (K. Liu, J. Xu, and X. C. Zhang, Appl. Phys. Lett., Vol. 85, pp. 863-865 (2004)). Thus, description is omitted here.

The advantages of the present technique over the Fourier-transform infrared spectroscopy are as follows.

(1) Simultaneous utilization of fingerprint spectra of absorption and refractive index (the absorption spectrum only, in Fourier-transform infrared spectroscopy) improves identification capability for a substance.

(2) Resolution enhancement and speedup can be achieved simultaneously. The resolution enhancement improves substance identification capability.

(3) Signal detection is performed by an coherent time-gating detection method (an electro-optical crystal or abundant a photoconductive antenna). This permits high-sensitivity and high-SN ratio measurement free from influence of thermal background noise which is specific to a thermal-type infrared detector generally used in Fourier transform infrared spectroscopy.

By virtue of these features (1) to (3) and the abundance of databases of infrared region fingerprint spectra, the present invention can be used in various applications.

EXAMPLE 4

In Example 4, in place of spectrometry in the frequency domain, application to a high-speed/deep-permeation terahertz cross-sectional imaging apparatus (THz tomography) is described, which is an application where the feature of high-speed acquisition of temporal waveform in the high-resolution/high-speed terahertz spectrometer according to the present invention is fully utilized.

Nondestructive internal inspection is an important measuring technique for various applications. Until now, X-ray diagnosis and ultrasonic diagnosis have been put to practical use. The former has high invasiveness, while the latter is contact measurement. Thus, their applications are restricted. The THz tomography is a typical measurement technique in which the features (free-space propagation, satisfactory permeability, low scattering, noninvasiveness, ultrashort pulses, and satisfactory beam directivity) of a THz pulse are fully utilized. In the THz tomography, a two-dimensional cross-sectional image is obtained in a non-contact/remote and non-invasive manner and with a high spatial resolution. Accordingly, this method is a promising candidate for internal inspection means that replaces the conventional methods including an ultrasonic echo method, in the fields of living body diagnosis, non-destructive inspection, and the like.

However, the THz tomography according to a conventional method is based on a point-by-point measurement. Thus, a scanning mechanism in several axes is necessary for acquiring the image, and hence a restriction has been placed on the real-time properties of measurement. For example, in order to acquire a two-dimensional cross-section image of a sample, two-axial scanning in time delay and sample position is necessary. Since the two-dimensional information is measured serially by performing a scan, a measuring time from several minutes to several hours has been necessary in the acquisition of a single image.

As means for reducing such a long measuring time, the present invention is effective. FIG. 21 shows a block diagram. The optical sampling light source controlling unit and the SFG cross correlation measuring unit are similar to those of Example 1 (FIG. 11). The terahertz optical system is changed from a conventional transmission arrangement into a reflection arrangement. A THz pulse emitted from the photoconductive switch for terahertz generation (or the nonlinear optical crystal) is collimated by the lens. After that, a part of it is reflected by a beam splitter. The reflected THz pulse is focused by the lens and then projected onto the sample.

The THz echo pulse sequence separated in time by the internal structure (group refractive index) of the sample is focused and collimated by the lens and after that, transmitted through the beam splitter. Finally, when the THz echo pulse sequence and the probe light are incident onto the photoconductive switch for THz detection, high-speed sampling measurement is achieved on the temporal waveform of THz electric field. From the obtained temporal waveform, information on internal structure in the sample along the depth direction is acquired. When the sample is scanned further in the transverse direction, a two-dimensional cross-section image is obtained.

The merits of the present technique over the conventional THz tomography are as follows.

(1) By virtue of the high-speed acquisition of temporal waveform, a mechanical scanning mechanism is necessary only in sample scanning. This remarkably reduces the final measuring time.

(2) By virtue of the use of a remarkably large measuring time window (12 ns in FIG. 14($a$)), high-speed measurement can be performed to a rather deep part (an applicable depth of 1.2 meters when the group refractive index of the sample is 1.5). This permits effective utilization of the good permeability of the THz pulse.

(3) By virtue of the signal accumulation processing (FIG. 15) in the high-speed sampling measurement, even a weak THz pulse echo signal can be measured with a satisfactory measurement SN.

INDUSTRIAL APPLICABILITY

The high-resolution/high-speed terahertz spectrometer according to the present invention is applicable to a frequency analyzer (decoder) in THz wavelength multiplex communication in next-generation information communication. As an example of its application, THz communication in space which utilizes satisfactory directivity of the THz pulse can be expected. Interception from the earth is impossible owing to a strong THz absorption by water vapor in air. Thus, this application is interesting as space communication means with high concealment.

Further, the possibility exists that the present invention can be used as a frequency standard measurement device in the terahertz band that bridges light waves and electric waves. Other possible applications are: a evaluating device of physical property for semiconductor and other materials by means of high-resolution terahertz time-domain spectrometry (or high-resolution infrared time-domain spectrum); and medical diagnosis and non-destructive inspection techniques by means of high-speed/deep-permeation THz tomography.

Figure 1:
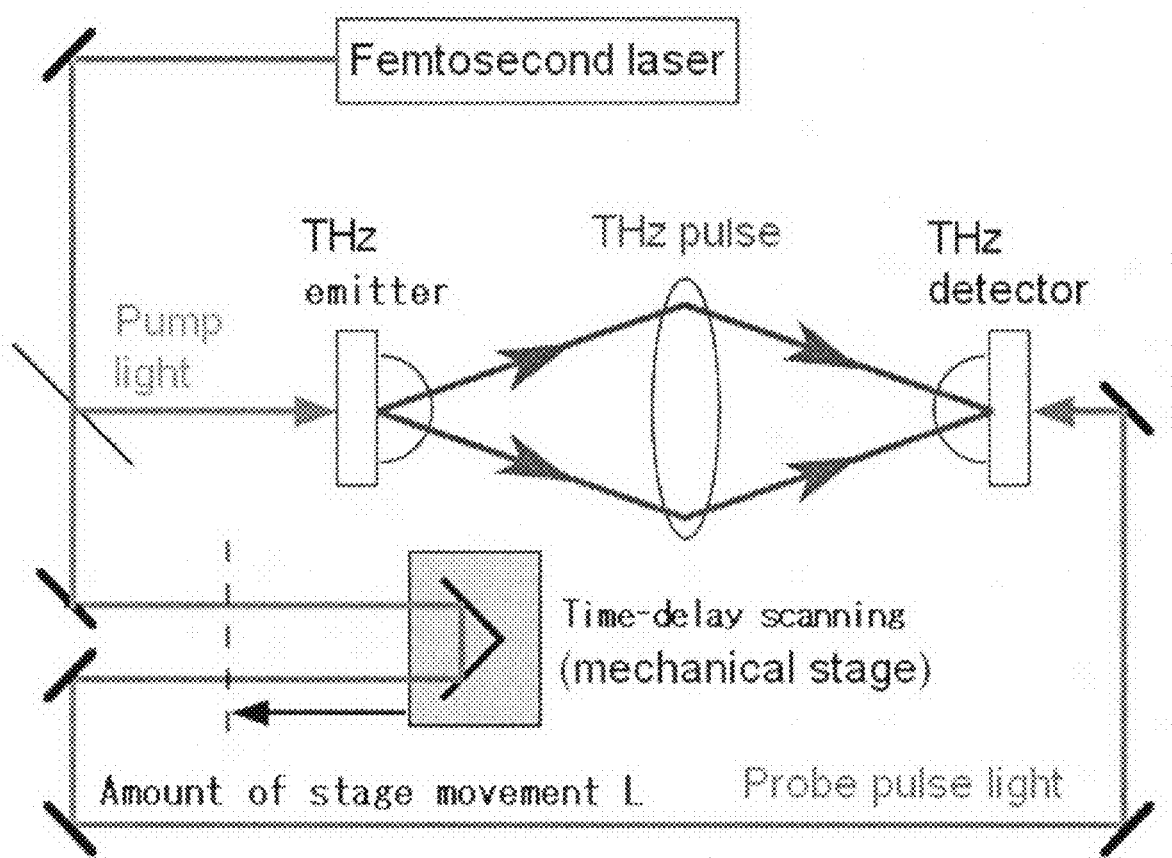
FIG. 1 is a configuration diagram of a general measuring device employing THz-TDS method.
Figure 2:
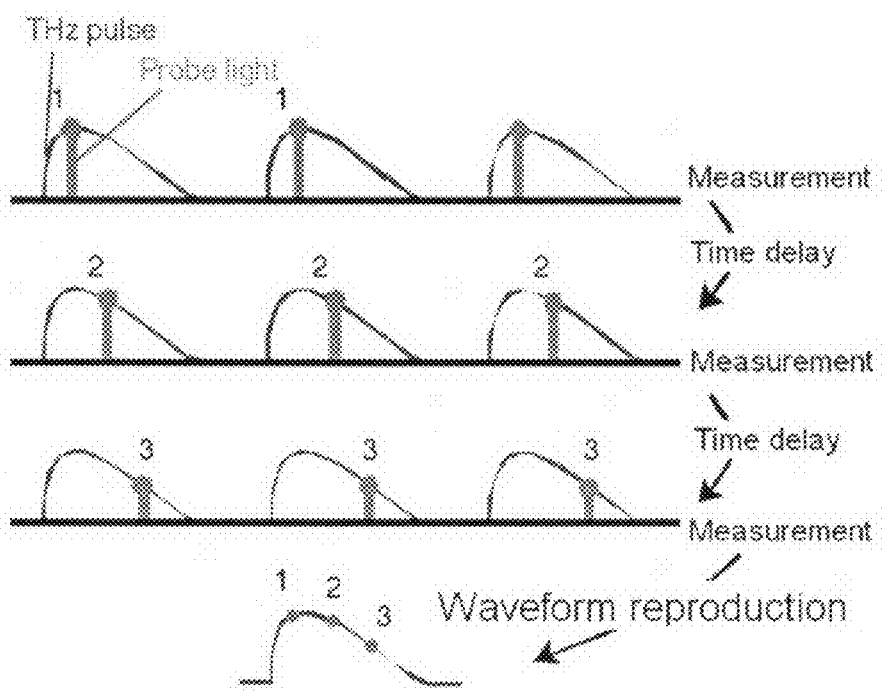
FIG. 2 is a schematic diagram describing a situation that in a measuring device employing a THz-TDS method, time-delay scanning is performed by a mechanical stage so that a temporal waveform of THz electric field is reproduced.
Figure 3:
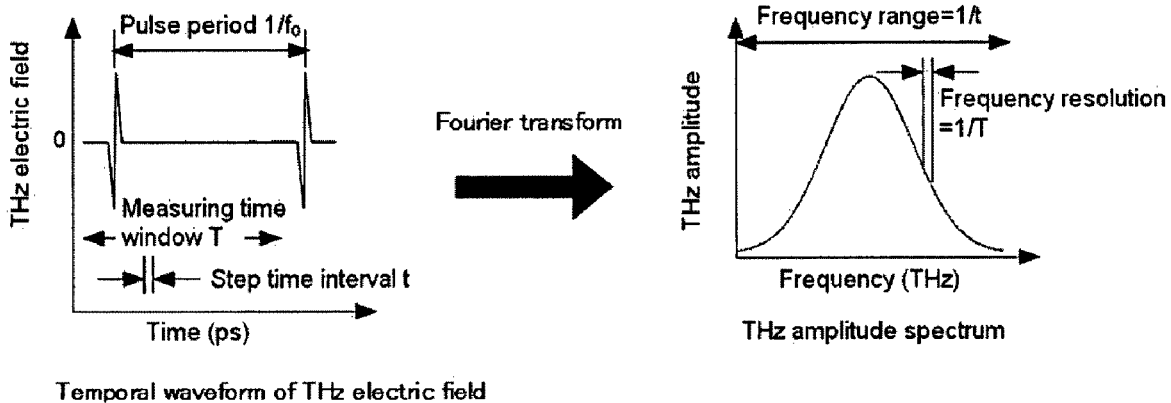
FIG. 3 shows the frequency spectrum of the THz amplitude obtained by performing, with a computer, Fourier transform on the temporal waveform of a measured THz electric field.
Figure 4:
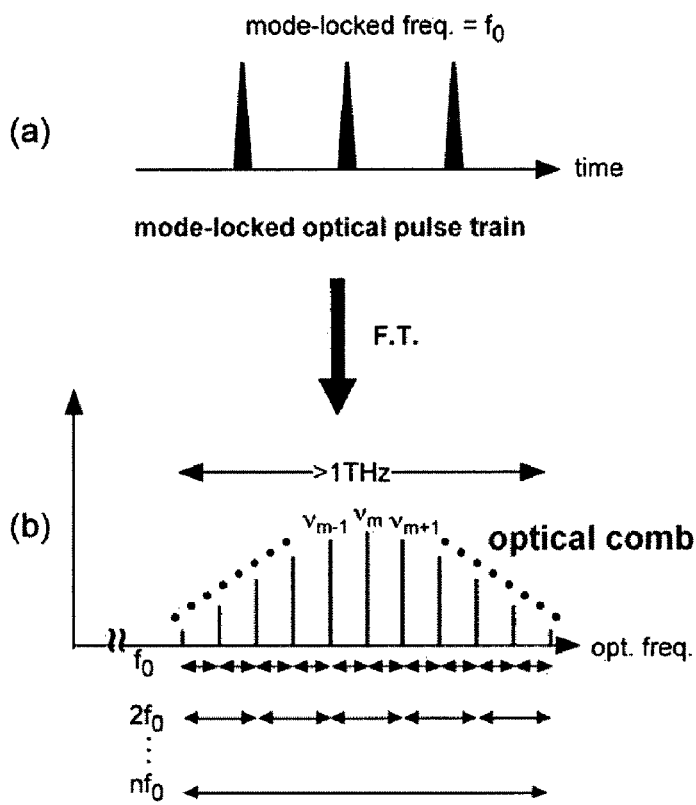
FIG. 4 is a schematic diagram of a spectrum structure of an optical comb aligned regularly at intervals of a mode-locked frequency ($=f_0$).
Figure 5:
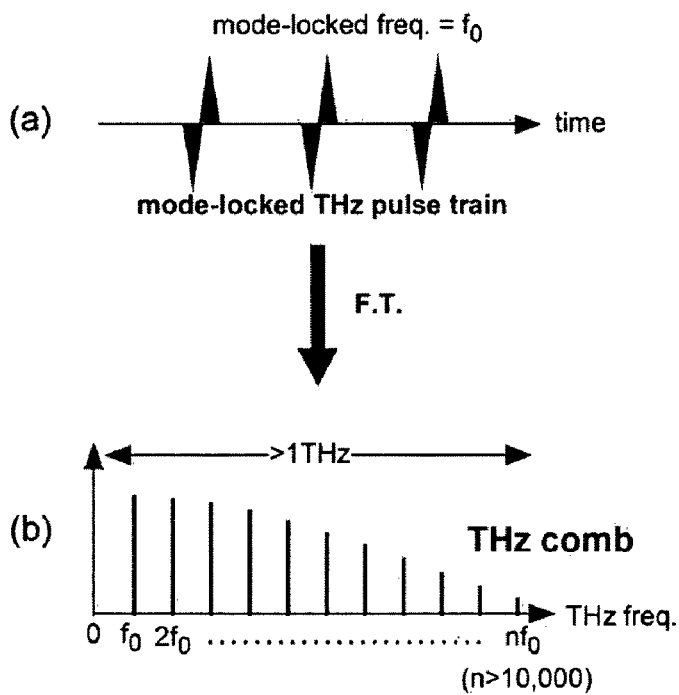
FIG. 5 is a schematic diagram of a spectrum structure of a THz comb aligned regularly at intervals of a mode-locked frequency ($=f_0$).
Figure 6:
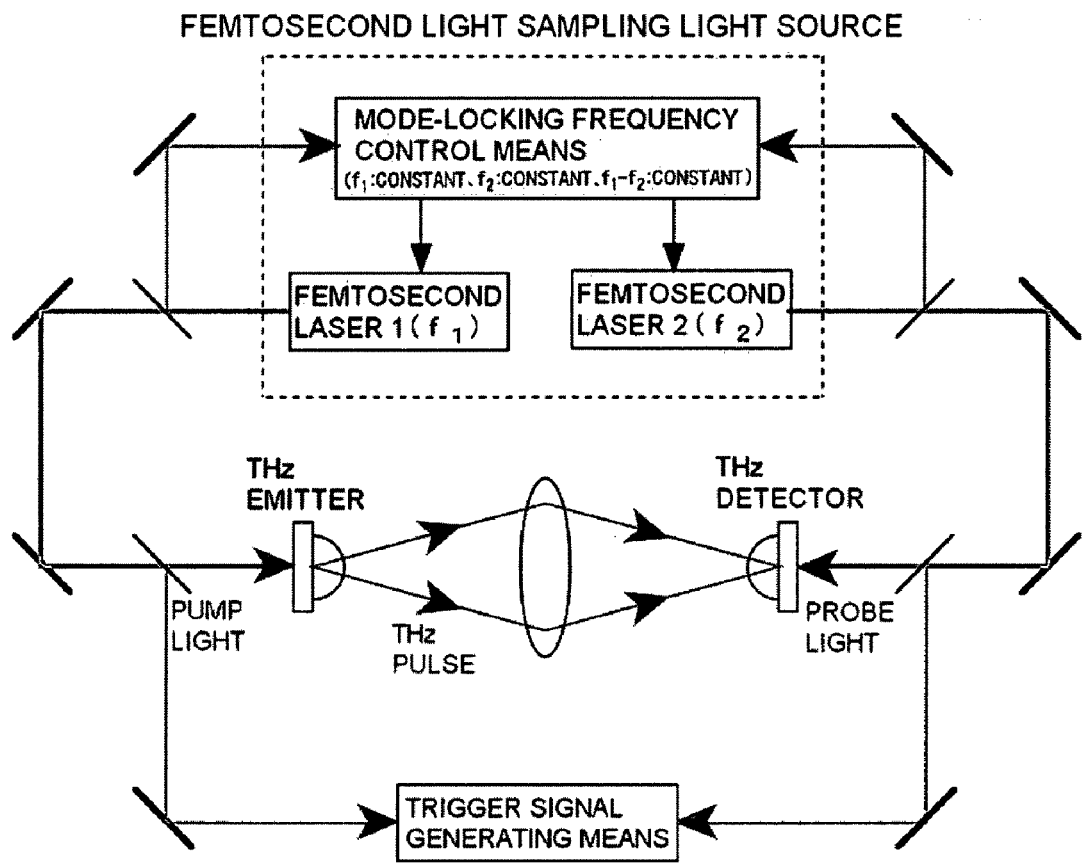
FIG. 6 is a configuration diagram of a high-resolution terahertz spectrometer according to the present invention.
Figure 7:
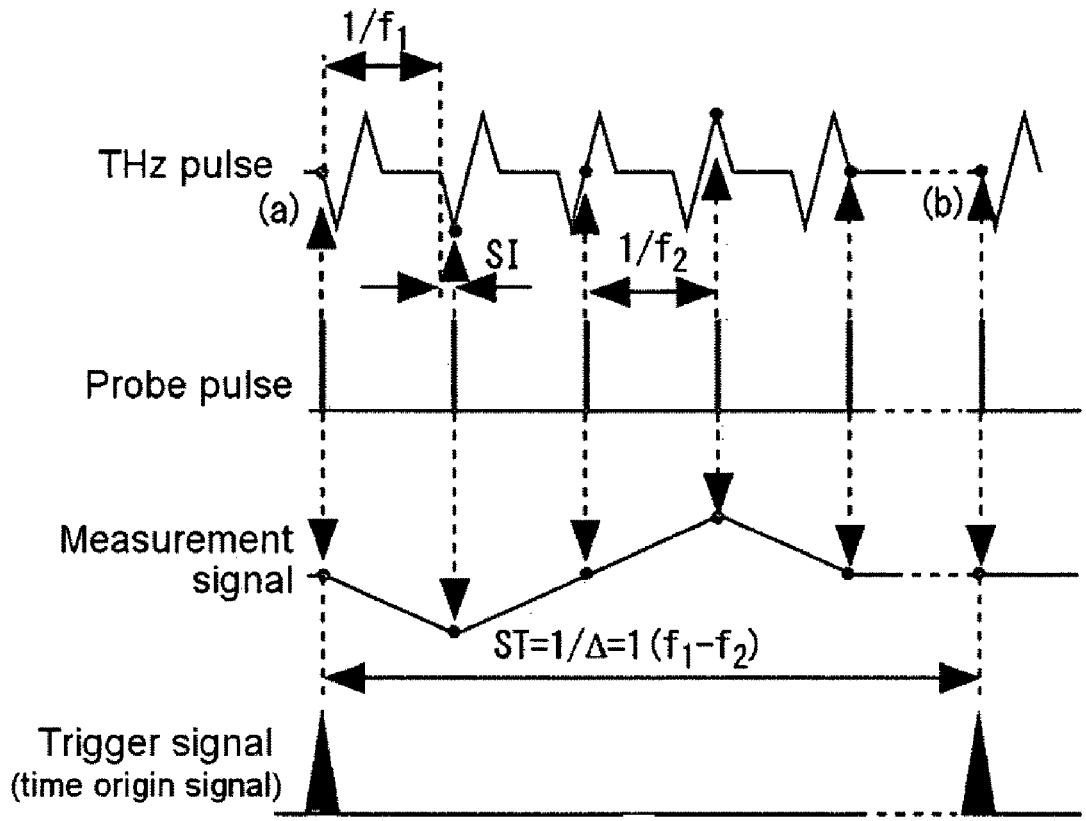
FIG. 7 is a schematic diagram describing a situation that a temporal waveform of a pulsed THz electric field is reproduced in a high-resolution terahertz spectrometer according to the present invention.
Figure 8:
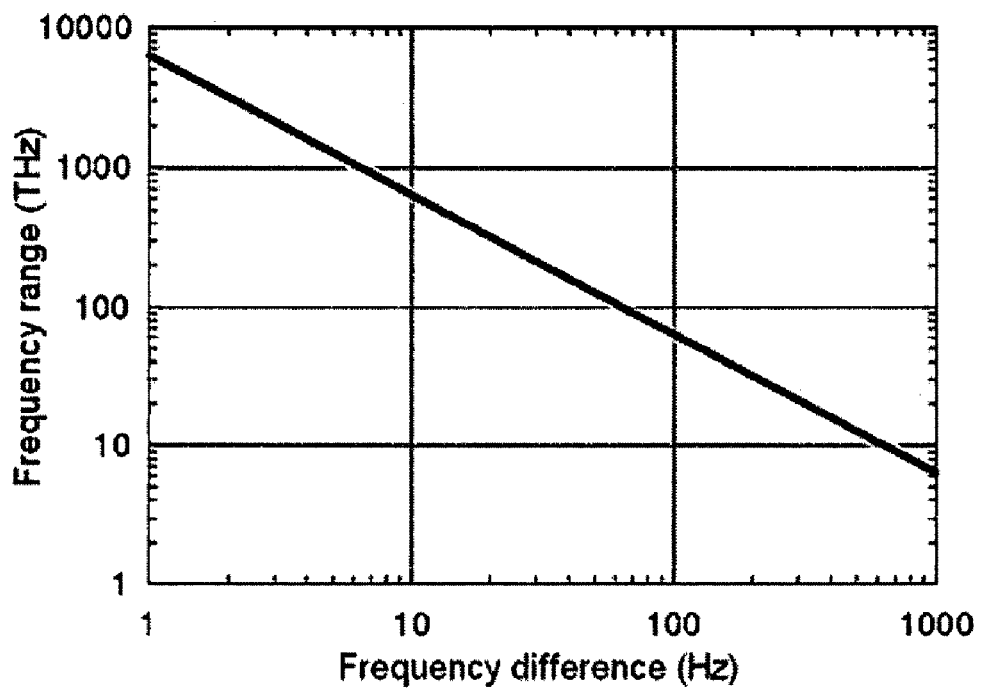
FIG. 8 is a relationship between the mode-locked frequency difference and the frequency range.
Figure 9:
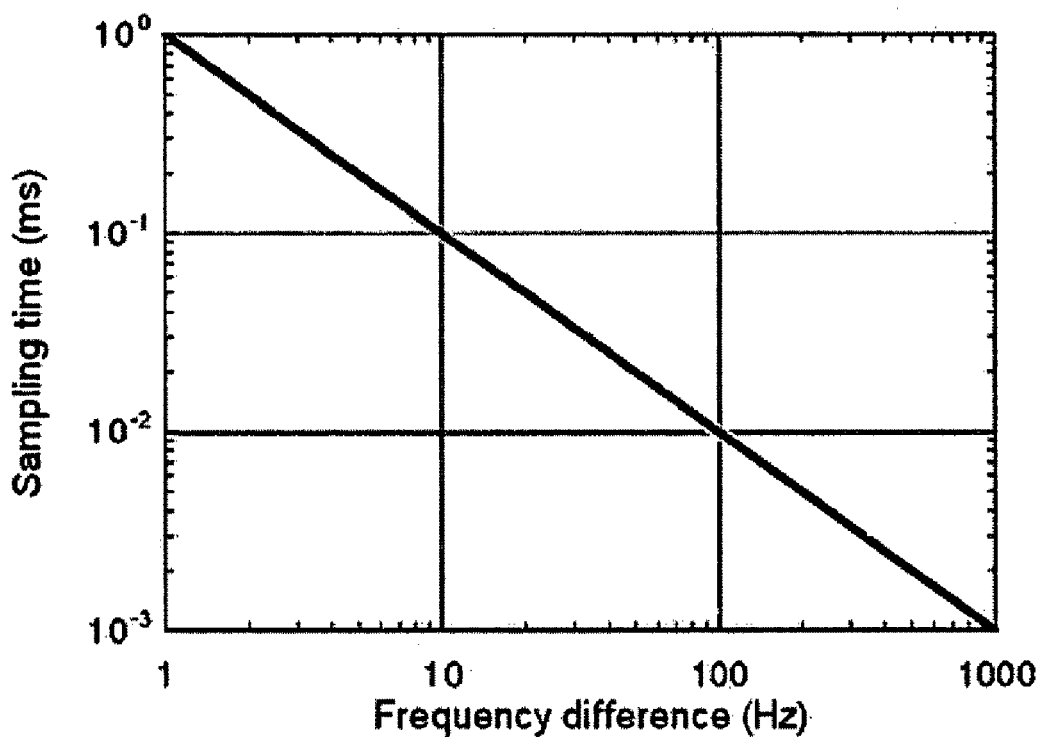
FIG. 9 is a relationship between mode-locked frequency difference and the sampling time.
Figure 10:
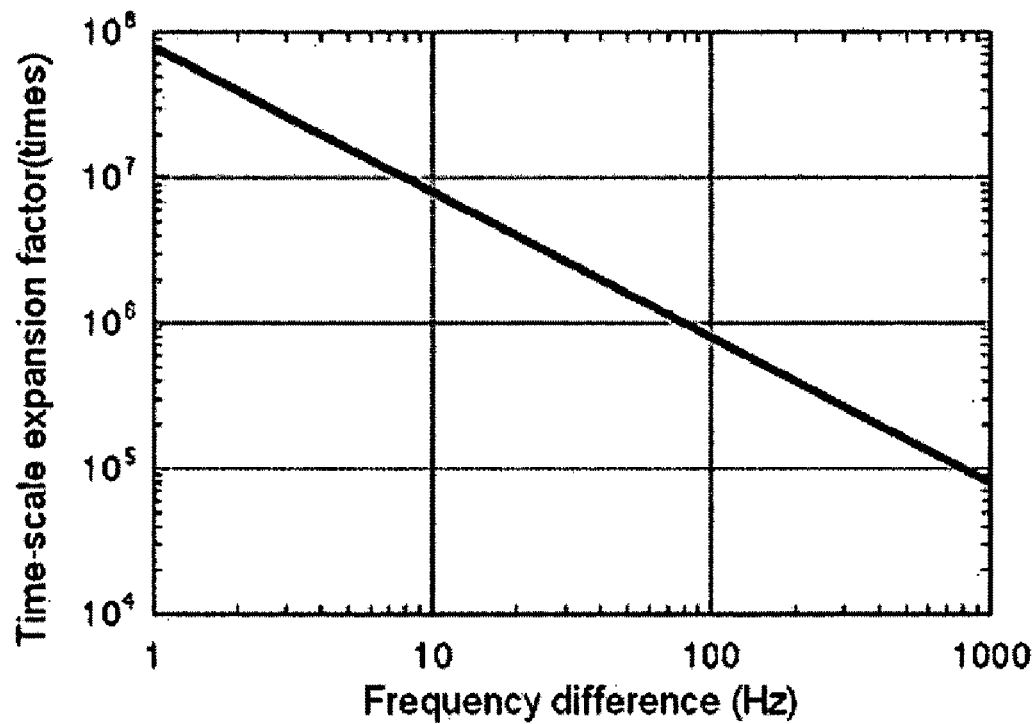
FIG. 10 is a relationship between the mode-locked frequency difference and the time scale expansion factor.
Figure 11:
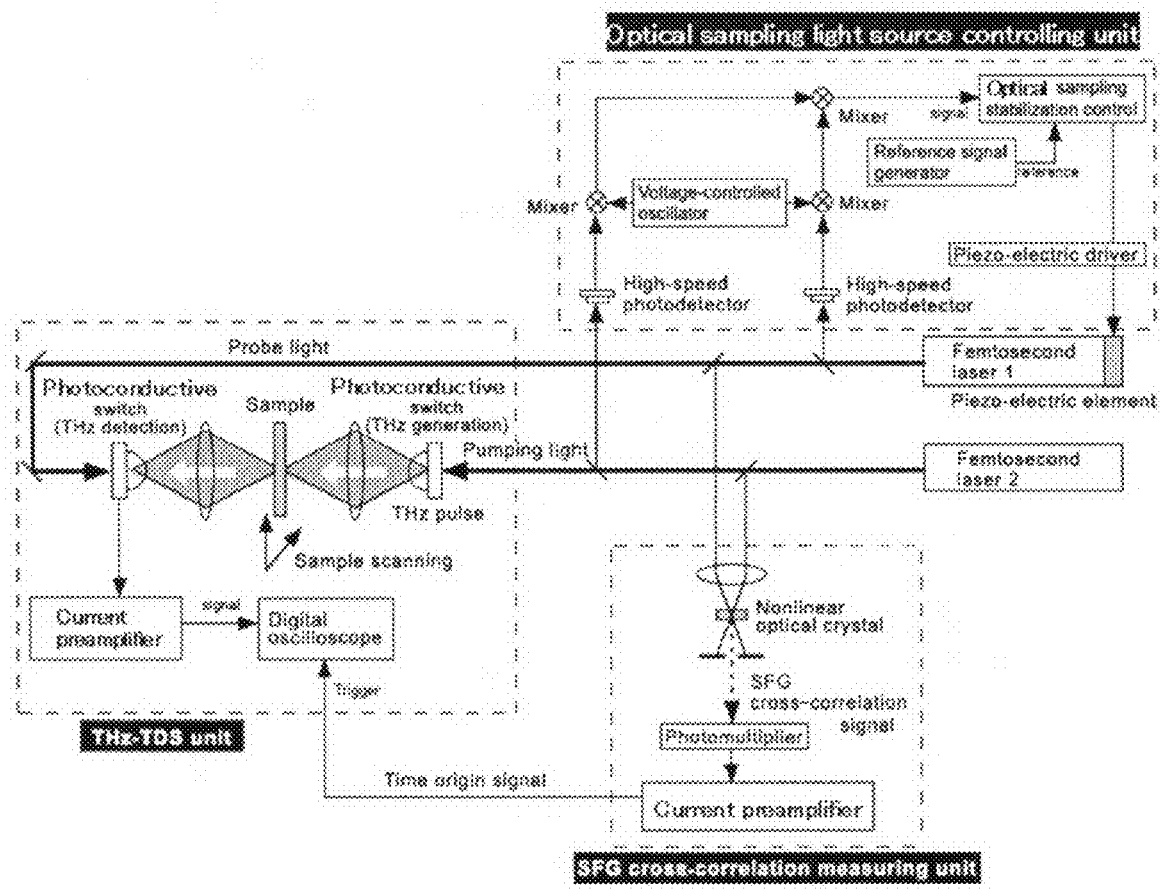
FIG. 11 is a block diagram of a high-resolution terahertz spectrometer according to Example 1.
Figure 12:
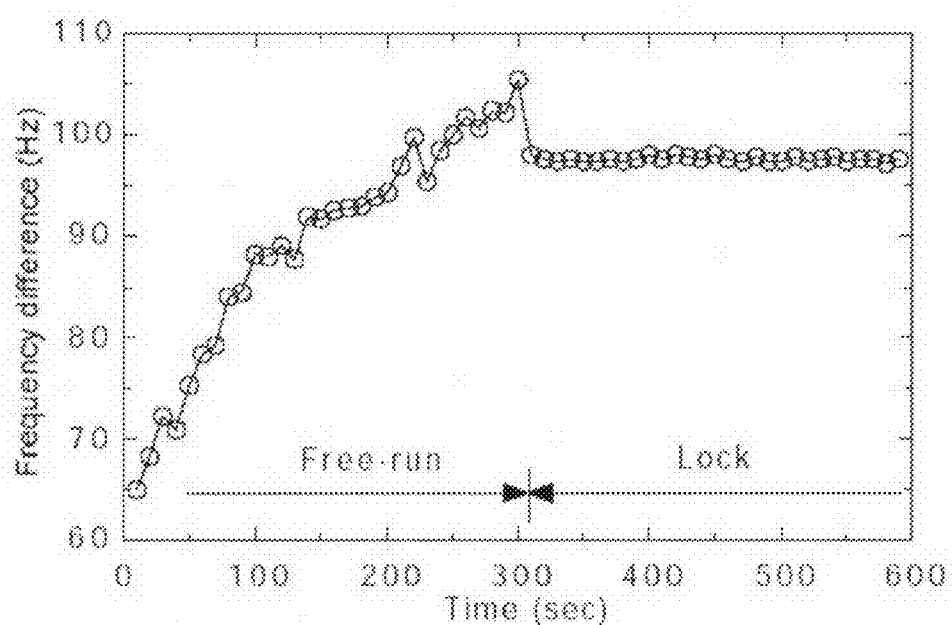
FIG. 12 is a diagram showing a temporal fluctuation of the difference frequency between mode-locked frequencies of two laser before and after the locking in a high-resolution/high-speed terahertz spectrometer according to Example 1.
Figure 13:
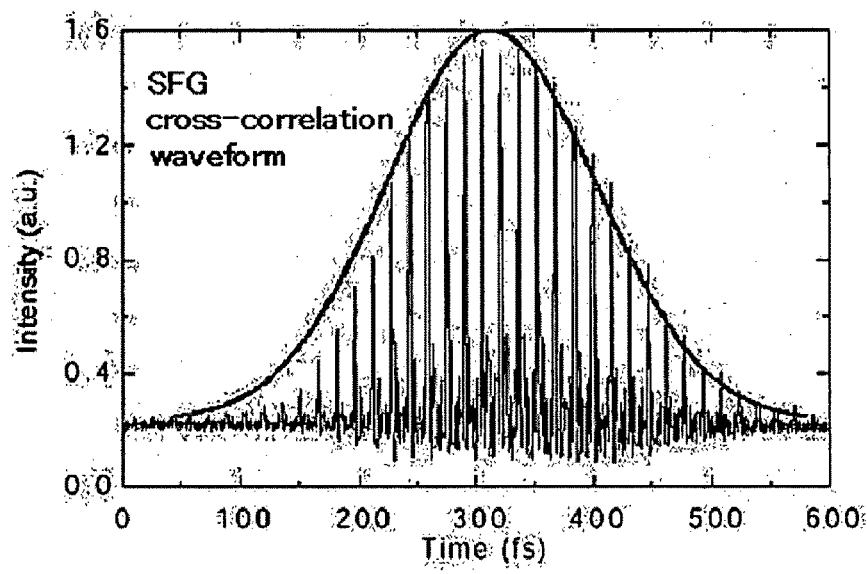
FIG. 13 shows an SFG cross-correlation signal waveform of two lasers in a high-resolution/high-speed terahertz spectrometer according to Example 1.
Figure 14:
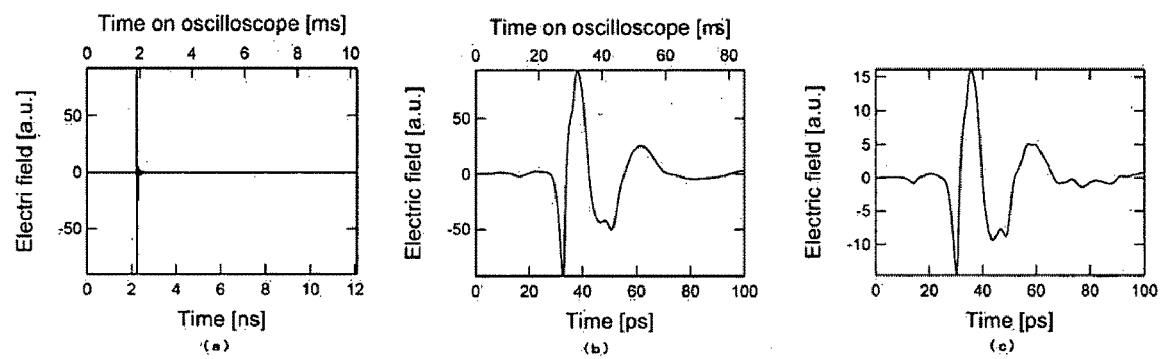
FIG. 14 shows a comparison between temporal waveform of a THz electric field by a high-resolution/high-speed terahertz spectrometer according to Example 1 and that acquired by a conventional THz-TDS system using a mechanical stage. (a) High-resolution/high-speed terahertz spectrometer (12 ns in full scale), (b) High-resolution/high-speed terahertz spectrometer (100 ps in full scale), and (c) conventional THz-TDS (100 ps in full scale).
Figure 15:
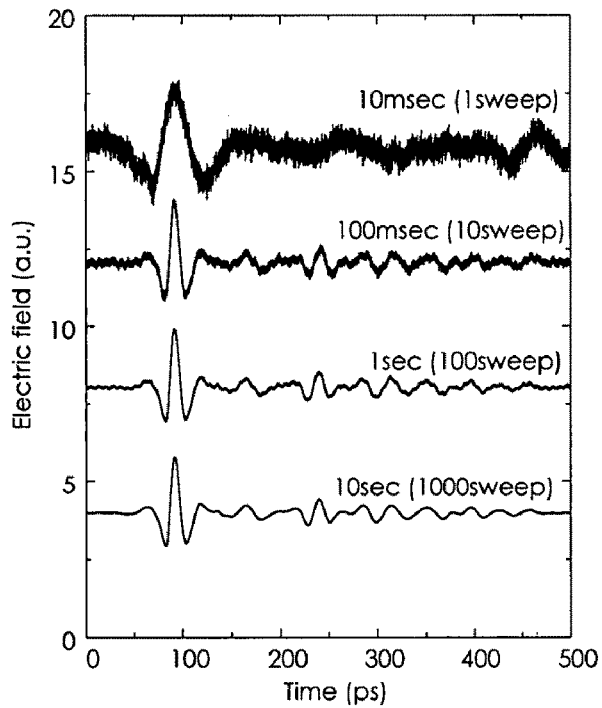
FIG. 15 shows a change in the measuring time (number of times of accumulation) for a THz electric field time wave obtained by a high-resolution/high-speed terahertz spectrometer according to Example 1.
Figure 16:
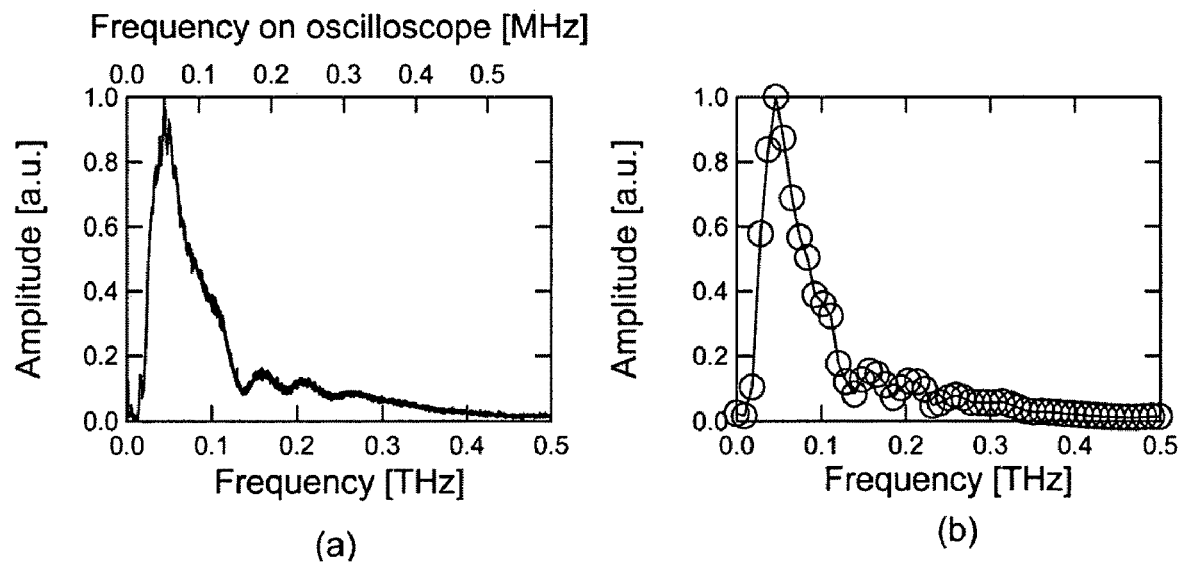
FIG. 16 shows a comparison between a THz amplitude spectrum acquired by a high-resolution/high-speed terahertz spectrometer according to Example 1 and that by a conventional THz-TDS system using a mechanical stage. (a) High-resolution/high-speed terahertz spectrometer and (b) conventional THz-TDS.
Figure 17:
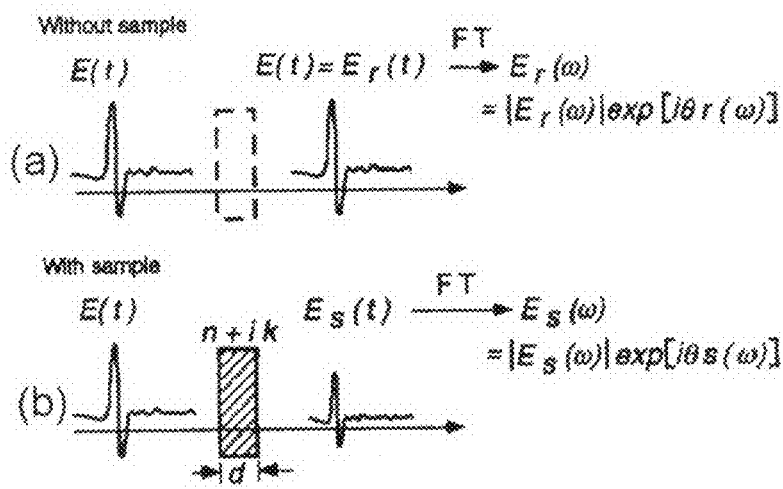
FIG. 17 is a schematic diagram describing a mechanism of performing component analysis using THz amplitude and phase spectra obtained by Fourier transform of a temporal waveform of a THz pulse.
Figure 18:
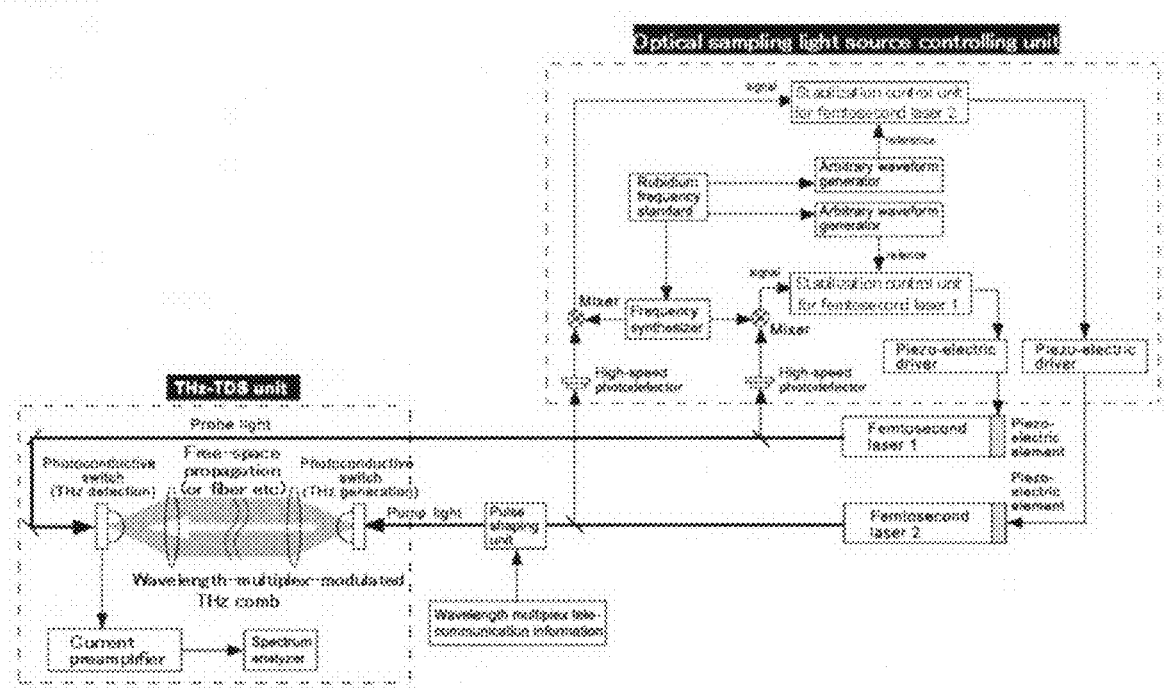
FIG. 18 is a block diagram of ultra-broadband wavelength multiplex THz information communication according to Example 2.
Figure 19:
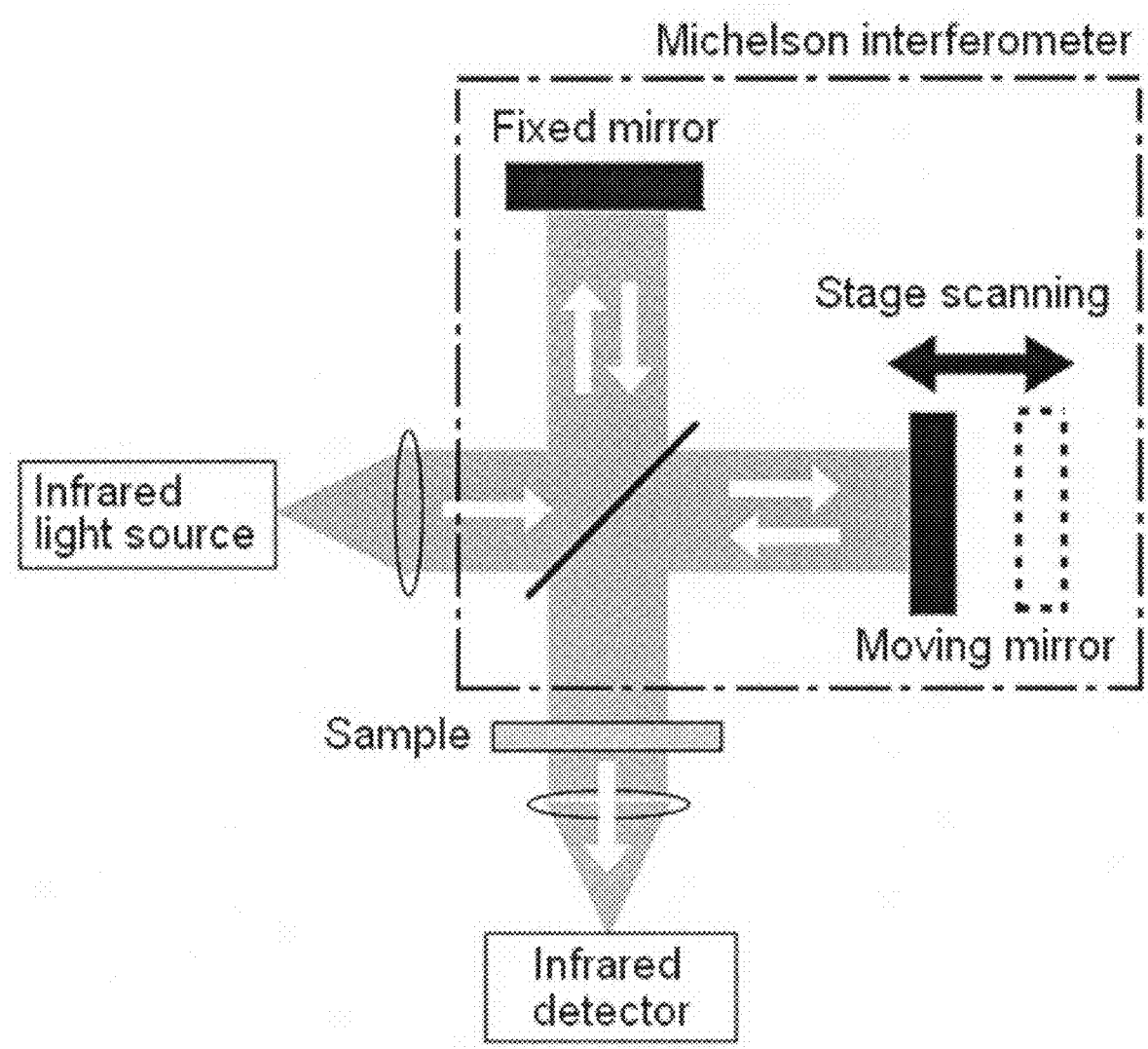
FIG. 19 is a block diagram of a general Fourier transform infrared spectrometer.
Figure 20:
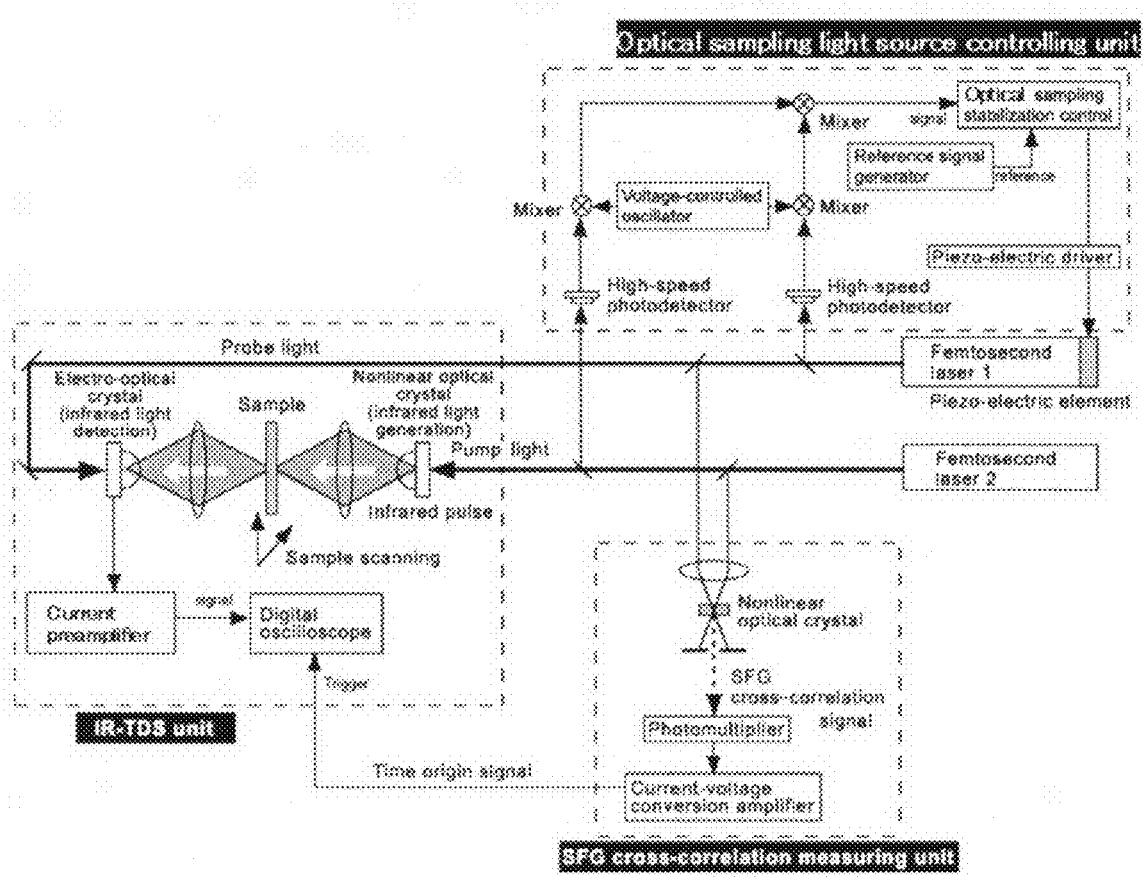
FIG. 20 is a block diagram of high-resolution/high-speed infrared time-domain spectroscopy according to Example 3.
Figure 21:
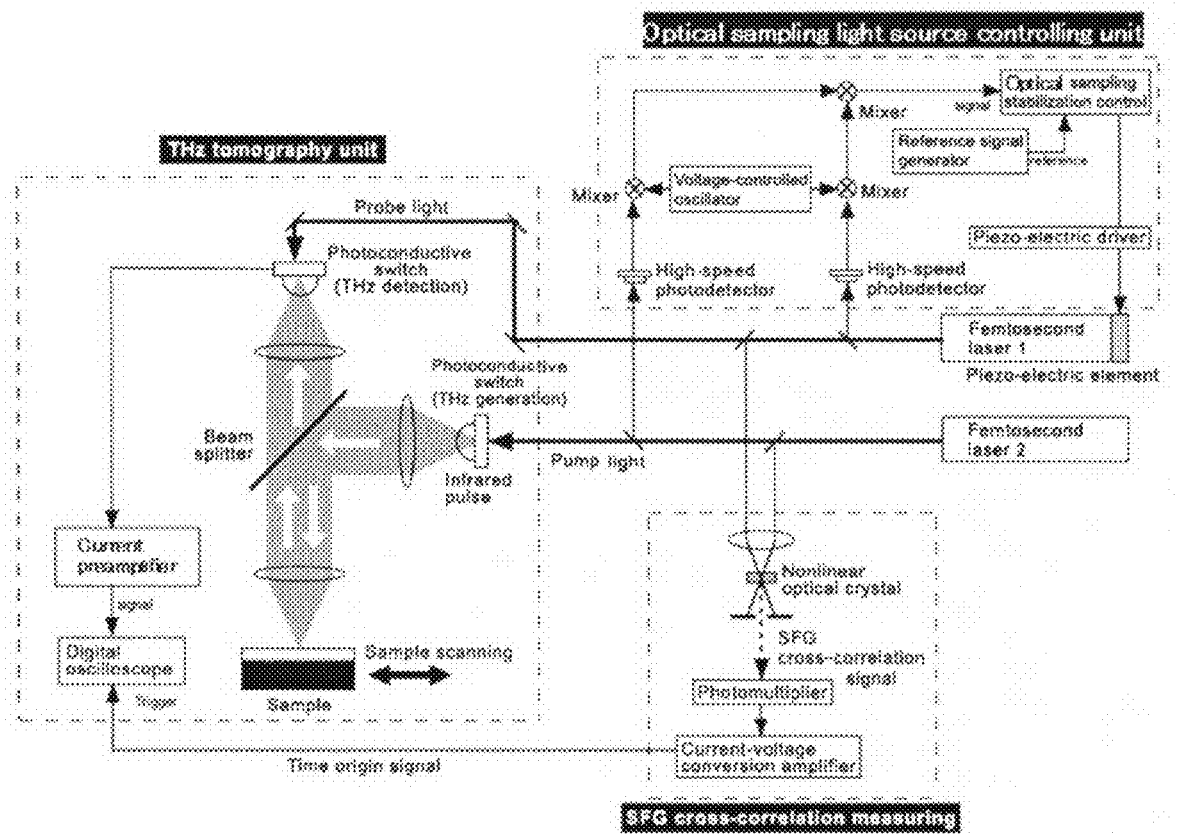
FIG. 21 is a block diagram of high-speed/deep-permeation THz tomography according to Example 4.

The invention claimed is:

1. A terahertz spectrometer comprising:
(a) two units of femtosecond laser means each having a laser repetition rate (mode-locked frequency) different from each other;
(b) mode-locked frequency controlling means for controlling the two units of femtosecond laser means at the same time independently each such that the mode-locked frequency of each of the two units of femtosecond laser means is stabilized and the difference in the mode-locked frequencies is held at a predetermined fixed value;
(c) terahertz wave radiating means for emitting a terahertz electromagnetic pulse by using output light of one femtosecond laser as excitation light and by using a photoconductivity switch or a nonlinear optical crystal;
(d) terahertz wave optical system means for irradiating a sample for spectroscopy with a terahertz electromagnetic pulse emitted from the terahertz wave radiating means and further guiding the terahertz electromagnetic pulse influenced by the sample;
(e) terahertz wave detecting means for detecting an temporal waveform of electric field of the terahertz electromagnetic pulse by using output light of the other femtosecond laser as probe pulse light, by making incident the terahertz electromagnetic pulse and probe pulse light, and by using a photoconductive switch or an electro-optical sampling method;
(f) trigger signal generating means for generating a time origin signal by extracting a part of the output light of the two units of the femtosecond laser means; and
(g) signal waveform measuring means by detecting in synchronization a signal waveform of the terahertz electromagnetic pulse, by amplifying the weak electric signal outputted from the terahertz wave detecting means and by using as a time origin signal the signal outputted from the trigger signal generating means.

2. The terahertz spectrometer according to claim 1, wherein the mode-locked frequency controlling means performs control by using as a reference signal an electric signal outputted from a frequency standard device and by using as a control signal a fundamental component or a higher harmonic components of the mode-locked frequency.

3. The terahertz spectrometer according to claim 2, wherein the frequency standard device is a rubidium frequency standard device or a cesium frequency standard device.

4. The terahertz spectrometer according to claim 1, wherein the trigger signal generating means is a device for extracting a part of the output light of the two units of the femtosecond laser means, non-collinearly focusing the light onto a nonlinear optical crystal, and performing photoelectric conversion of the generated SFG (sum frequency generation light) cross-correlation signal light so as to output the light.

5. The high-resolution high-speed terahertz spectrometer according to claim 1, further comprising
(h) signal analyzing means for acquiring frequency analysis information of a sample from a high-resolution Fourier spectrum (frequency spectrum in amplitude and phase) obtained by performing time-scale conversion and Fourier transform of temporal waveform of THz electric field outputted from the signal waveform measuring means.

6. The terahertz spectrometer according to claim 1, wherein the mode-locked frequency controlling means is controlling means for a cavity length of the femtosecond laser.

7. The terahertz spectrometer according to claim 1, wherein a frequency range, a sampling time, or a time-scale expansion factor can be set arbitrarily by selecting the value of the frequency difference held by the mode-locked frequency controlling means.

* * * * *